United States Patent [19]

Cragoe, Jr. et al.

[11] 4,029,816

[45] June 14, 1977

[54] SUBSTITUTED 2-AMINOMETHYL-6-IODOPHENOLS

[75] Inventors: Edward J. Cragoe, Jr., Lansdale; Everett M. Schultz, Ambler, both of Pa.

[73] Assignee: Merck & Co., Inc., Rahway, N.J.

[22] Filed: Sept. 20, 1976

[21] Appl. No.: 724,896

Related U.S. Application Data

[63] Continuation-in-part of Ser. No. 635,198, Nov. 25, 1975, abandoned, which is a continuation of Ser. No. 466,316, May 2, 1974, abandoned, which is a continuation-in-part of Ser. No. 435,558, Jan. 22, 1974, abandoned, which is a continuation of Ser. No. 101,178, Dec. 23, 1970, abandoned.

[52] U.S. Cl. .................. 424/316; 260/433; 260/501.17; 260/501.19; 260/553 A; 260/558 R; 260/559 S; 260/562 A; 260/562 B; 260/570.9; 260/612 D; 260/623 R; 424/330

[51] Int. Cl.² ............ A01N 9/20; A01N 9/24; C07C 87/28

[58] Field of Search .............. 260/501.17, 501.19, 260/570.9; 424/316, 330

[56] References Cited

UNITED STATES PATENTS

| | | | |
|---|---|---|---|
| 2,220,835 | 11/1950 | Bruson et al. | 260/570.9 X |
| 3,082,113 | 3/1963 | Hemwall | 260/570.9 X |
| 3,781,359 | 12/1973 | Randall et al. | 260/570.9 |
| 3,794,734 | 2/1974 | Cragoe, Jr. et al. | 424/330 |
| 3,864,401 | 2/1975 | Cragoe, Jr. et al. | 260/570.9 |
| 3,928,624 | 12/1975 | Cragoe, Jr. et al. | 424/330 |

FOREIGN PATENTS OR APPLICATIONS

M3087  1/1965  France .................. 260/570.9

OTHER PUBLICATIONS

Miyoshi, "Jour. Chem. Soc. Ind. Japan," vol. 49, pp. 64–67 (1946).
Miyoshi, "Chemical Abstracts," vol. 42, p. 6154 (1948).
Arct et al., "Chemical Abstracts," vol. 61, pp. 3000–3081 (1964).

*Primary Examiner*—Robert V. Hines
*Attorney, Agent, or Firm*—Michael C. Sudol, Jr.; J. Jerome Behan

[57] ABSTRACT

Certain substituted 2-aminomethyl-6-iodophenols and their pharmaceutically acceptable acid addition salts wherein the phenyl nucleus may be further substituted with 1 to 3 nuclear substituents are useful as antihypertensive, diuretic and saluretic agents. These products may be prepared by either iodinating a 2-aminomethyl-3,4,5-substituted phenol or hydrolyzing an appropriately substituted N-(2-hydroxy-3-iodo-4,5,6-substituted benzyl)carboxamide under either acidic or basic conditions.

14 Claims, No Drawings

SUBSTITUTED 2-AMINOMETHYL-6-IODOPHENOLS

CROSS REFERENCE TO RELATED APPLICATIONS

This case is a continuation-in-part of co-pending application U.S. Pat. Ser. No. 635,198 filed Nov. 25, 1975 and now abandoned which itself is a continuation of now abandoned U.S. Pat. application, Ser. No. 466,316 filed May 2, 1974 which latter case is a continuation-in-part of now abandoned Ser. No. 435,558 filed Jan. 22, 1974 which itself is a continuation of U.S. Pat. Ser. No. 101,178 filed Dec. 23, 1970 now abandoned.

This invention relates to a new class of chemical compounds which can be described generally as substituted 2-aminomethyl-6-iodophenols and to their non-toxic pharmaceutically acceptable salts.

Pharmacological studies indicate that the instant products are effective antihypertensive, diuretic and saluretic agents which can be used in the treatment of conditions associated with electrolyte and fluid retention and hypertension. When administered in a therapeutic dosage in conventional vehicles, the instant products effectively reduce the amount of sodium and chloride ions in the body, lower dangerous excesses of fluid to acceptable levels and, in general, alleviate conditions usually associated with edema and hypertension. In comparison to other diuretics which are used in the treatment of hypertension, the instant products of this invention are unique in that they generally possess the advantage of intrinsic antihypertensive activity. Accordingly, their antihypertensive activity does not depend solely on their diuretic and saluretic properties. In addition, it is know known that the 6-iodo substituent plays a critically important role in the intrinsic antihypertensive activity displayed by the instant products since replacement of the 6-iodo group with other substituents, including fluoro, chloro and bromo, leads to either oblation or marked diminution of the intrinsic antihypertensive activity.

The substituted 2-aminomethyl-6-iodphenols of this invention are componds having the following structural formula (I):

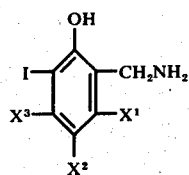

wherein $X^1$ is selected from the group consisting of hydrogen, methyl and methoxy; $X^2$ is lower alkyl containing from 3–5 carbon atoms such as propyl, 1-methylethyl, butyl, 1-methylpropyl, 2-methylpropyl, 1,1-dimethylethyl, pentyl, 1-methylbutyl, 12-methylbutyl, 3-methylbutyl, 1,1-dimethylpropyl, 1,2-dimethylpropyl, 2,2-dimethylpropyl and 1-ethylpropyl; and $X^3$ is selected from the group consisting of hydrogen, methyl, ethyl, methoxy and ethoxy. Also included are the non-toxic, pharmaceutically acceptable salts, preferably, the non-toxic, pharmaceutically acceptable acid addition salts derived from a non-toxic, pharmaceutically acceptable acid such as hydrochloric acid, hydrobromic acid, hydriodic acid, sulfuric acid, methanesulfonic acid, isethionic acid, phosphoric acid and the like. Likewise, the alkali metal salts may be prepared from the alkali metal bases such as sodium hydroxide, potassium hydroxide and the like.

A preferred embodiment of this invention relates to the substituted 2-aminomethyl-6-iodophenols having the following structural formula:

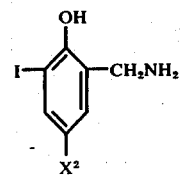

wherein $X^2$ is as defined above and the non-toxic, pharmaceutically acceptable acid addition salts thereof. This class of compounds exhibits particularly good antihypertensive, diuretic and saluretic activity and repesents a preferred subgroup of compounds within the scope of this invention.

A most preferred embodiment of this invention is that group of substituted 2-aminomethyl-6-iodophenols wherein $X^2$ is a 4 or 5 carbon atom branched alkyl chain, particularly where the branch point in $X^2$ is situated on the carbon atom attached to the aromatic ring such as in the 1,1-dimethylethyl group and the like and the non-toxic pharmaceutically acceptable acid addition salts thereof.

The substituted 2-aminomethyl-6-iodophenols of this invention may be prepared by two synthetic methods as described in detail below.

METHOD A

This general synthetic method is useful for the preparation of the substituted 2-aminomethyl-6-iodophenols represented by Formula I:

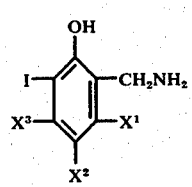

wherein $X^1$, $X^2$ and $X^3$ are as previously defined.

In this method, a substituted 2-aminomethylphenol (II) hydrochloride is treated with a suitable iodination reagent such as iodine monocloride or 1,3-diiodo-5,5-dimethylhydantoin, preferably the former, in a suitable protic acidic medium, preferably 3N hydrocloric acid, at ° to 80° C, preferably between 20° and 30° C, for a period ranging from 1 to 10 hours, preferably 2 to 4 hours, to provide the desired products I as their hydrochloride salts. This reaction is illustrated in the equation below:

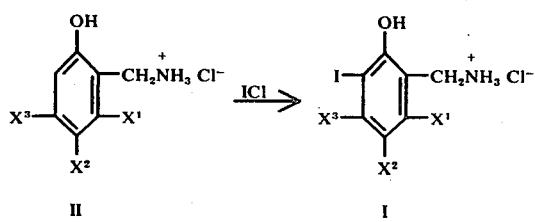

| II | I | wherein $X^1$, $X^2$ and $X^3$ are as previously defined. It should be noted that I hydrochlorides shown above are readily converted to the corresponding free amines of I using known neutralization methods as described below. Treatment of an aqueous solution of the I hydrochloride with a suitable base, preferably a slight molar excess, such as ammonium hydroxide, sodium bicarbonate, potassium bicarbonate and the like, preferably ammonium hydroxide, at or about room temperature provides the corresponding free amine of I as indicated in the equation below:

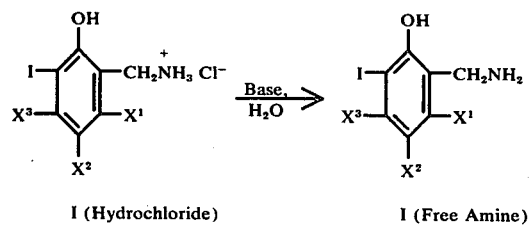

I (Hydrochloride)   I (Free Amine)

wherein $X^1$, $X^2$, and $X^3$ are as previously defined.

The free amines of I are readily converted to either the corresponding non-toxic pharmaceutically acceptable acid addition salts thereof or the corresponding alkali metal salts thereof as described in detail below. Addition of 1 molar equivalent of a non-toxic pharmaceutically acceptable acid such as hydrochloric acid, hydrobromic acid, hydriodic acid, sulfuric acid, methane sulfonic acid, isethionic acid, phosphoric acid and the like to a solution of the I free amine in a suitable solvent such as methanol, ethanol, 2-propanol and the like, preferably ethanol, at or about room temperature followed by either removal of the solvent under reduced pressure of dilution with ether affords the corresponding I acid addition salt as illustrated in the following equation:

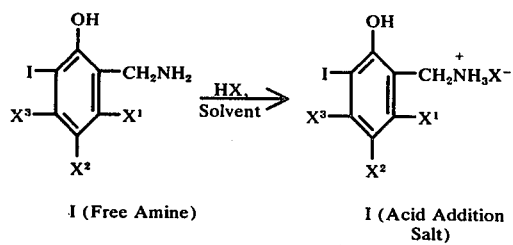

I (Free Amine)   I (Acid Addition Salt)

wherein $X^1$, $X^2$ and $X^3$ are as previously defined and $X^-$ is chloride, bromide, iodide, hydrogen sulfate, methane sulfonate, isethionate (i.e., 2-hydroxyethanesulfonate) or dihydrogenphosphate.

The corresponding I alkali metal salts are obtained by treating a solution of the I free amine in a suitable protic solvent, preferably methanol or ethanol, with an alkali metal hydroxide such as sodium hydroxide, potassium hydroxide and the like or an alkali metal alkoxide such as sodium methoxide, sodium ethoxide, potassium tert-butyloxide and the like followed by removal of the solvent in vacuo as shown in the equation below:

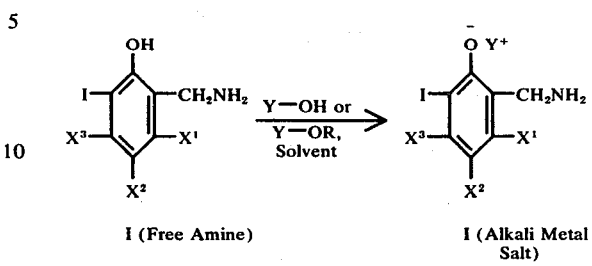

I (Free Amine)   I (Alkali Metal Salt)

wherein $X^1$, $X^2$ and $X^3$ are as peviously defined, Y is sodium or potassium and R is methyl or ethyl when Y is sodium and R is tert-butyl (i.e., 1,1-dimethylethyl) when Y is potassium.

The requisite intermediate substituted 2-aminomethylphenol hydrochloride (II) is obtained from an appropriately substituted N-(2-hydroxy-3,4,5,6-substituted benzyl)-carboxamide (III) via hydrolysis in an aqueous medium containing either a suitable acid, preferably a mineral acid such as hydrochloric acid, hydrobomic acid, hydroiodic acid, sulfuric acid and the like, or a suitable alkali base such as sodium hydroxide, potassium hydroxide and the like. In the latter case, terminal acidificaion with hydrochloric acid is necessary to convert the free amine of I to the desired hydrochloride salt. This hydrolysis is effected at a temperature between 20° to 110° C, preferably at the reflux temperature of the aqueous medium employed, for a period of 15 minutes to 5 hors, preferably about 1½ hours. When $X^4$ is chloro or bromo, as shown in IIIb below, the hydrolysis described above is followed by hydrogenolysis of the halo substituent in the presence of a suitable catalyst such as 5% palladium/carbon and the like at room temperature in a Parr apparatus at a pressure of about 30 p.s.i. to afford the desired II after acidificaion with HCl. The reaction is conducted in the presence of a base, such as sodium hydroxide and the like. These reactions are illustrated in the following equations:

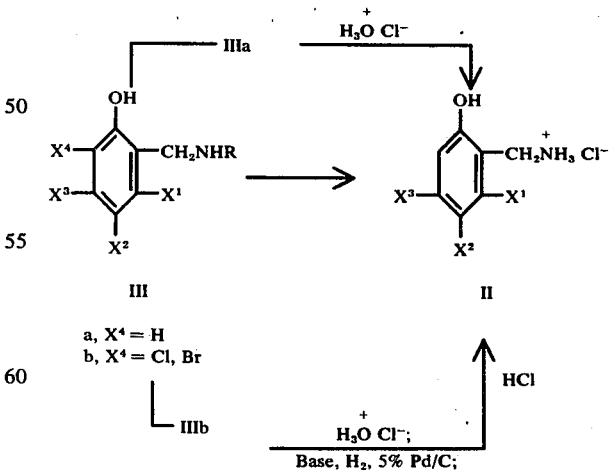

III   II a, $X^4 = H$
b, $X^4 = Cl, Br$ wherein $X^1$, $X^2$ and $X^3$ are as previously defined; $X^4$ is hydrogen in IIIa and bromine or chlorine in IIIb; and R is an acyl radical, for example, formyl, haloacetyl such as chloroacetyl and the like, carbamoyl, mononuclear aroyl such as benzoyl and the like, hydroxy substituted mononuclear aroyl such as o-hydroxybenzoyl and the like, and trihalomethylcarbonyl such as trichloroacetyl and the like.

Th appropriately substituted N-(2-hydroxy-3,4,5,6-substituted benzyl)carboxamide III is prepared by treating a substituted phenol IV with an N-(hydroxymethyl)carboxamide, for exaple, n-hydroxymethylurea, 2-halo-N-(hydroxymethyl)acetamides such as 2-chloro-N-(hydroxymentyl)acetamide and the like, an N-(hydroxymethyl)mononuclear aryl carboxamide such as N-(hydroxymethyl)benzamide and the like, an N-(hydroxymethyl)hydroxy substituted aryl carboxamide such as N-(hydroxymethyl)salicylamide and the like or an M-(hydroxymethyl)trihaloacetamide, such as N-(hydroxymethyl)-trichloroacetamide and the like, in the presence of a suitable mineral acid such as hydrochloric acid, sulfuric acid and the like. The amidomethylation reaction may be carried out using an excess of the mineral acid as the solent or with the aid of a solvent which is either inert or substantially inert to the reactants employed, for example, a lower alkanol such as ethanol and the like or a lower alkanoic acid such as acetic acid and the like. This process is illustrated in the following equation:

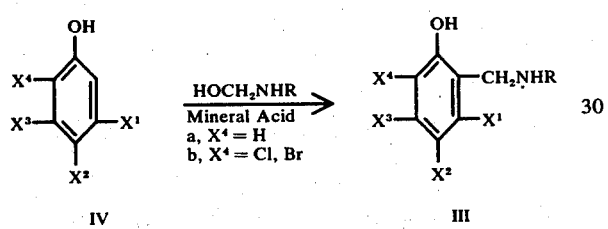

IV ⟶ III wherein $X^1$, $X^2$, $X^3$, $X^4$ and R as previously defined. In addition, it is to be noted that $X^4$ is hydrogen in IVa and $X^4$ is bromo or chloro in IVb. It is obvious to those skilled in the art that use of IVb in the above reaction can only yield the corresponding III, whreas, only those members of the IVa group bearing the proper orienting groups lead to the corresponding III, i.e., when $X^1$ is the same as $X^3$ and when $X^3$ is hydrogen while $X^1$ is either methoxy or methyl.

Finally, those starting phenols, IV, not currently known in the art but required for their ultimate conversion to the instant products of this invention can be prepared by the following method. Phenols of type V can be reacted with isobutylene in the presence of a suitable acid catalyst such as sulfuric acid and the like in an inert solvent such as benzene, methylene chloride and the like at a temperature of −10° to 40° C, preferably 20° to 25° C, for a period of 2 to 24 hours, preferably 4 to 8 hours, to afford phenols IV in which $X^2$ is the 1,1-dimethylethyl moiety as shown in the equation below:

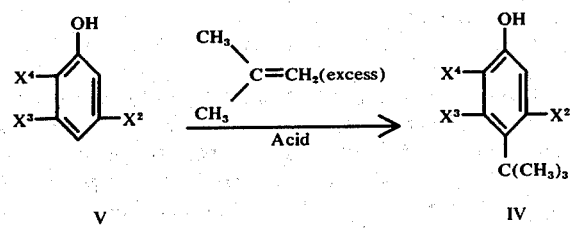

V ⟶ IV wherein $X^2$, $X^3$ and $X^4$ are as previously defined. The above reaction is particularly attractive for preparing certain substituted phenols such as 2-chloro-4-(1,1-dimethylethyl)-5-methoxyphenol, 3,5-dimethyl-4-(1,1-dimethylethyl)phenol, 3,5-dimethoxy-4-(1,1-dimethylethyl)phenol and the like.

Typical of the instant products of this invention which may be prepared by general synthetic Method A are:

2-Aminomethyl-4-(1-dimethylethyl)-6-iodophenol hydrochloride;

2-Aminomethyl-4-(1,1-dimethylpropyl)-6-iodophenol hydrochloride;

2-Aminomethyl-3-methoxy-4-(1,1-dimethylethyl)-6-iodophenol hydrochloride.

METHOD B

This method can be used to prepare a sub-group of the title compounds represented by structural formula VI:

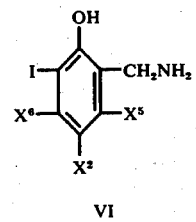

VI wherin $X^2$ is as previously defined in formula I; $X^5$ is the same as $X^6$ when $X^6$ is selected from the group consisting of hydrogen, methyl and methoxy; and in addition when $X^5$ is methyl or methoxy, $X^6$ can be hydrogen.

In this method, an appropriately substituted N-(2-hydroxy-3-iodo-4,5,6-substituted benzyl)carboxamide (VII) is hydrolyzed in an aqueous solution in the presence of an acid, preferably a mineral acid such as hydrochloric acid, hydrobromic acid, hydroiodic acid, sulfuric acid and the like. Likewise, hydrolysis of carboxamides VII to yield the substituted 2-aminomethyl-6-iodophenols (VI) can be effected in the presence of alkali metal bases such as sodium hydroxide, potassium hydroxide and the like. Any solvent, such as ethanol, acetic acid and the like, which is substantially inert to the reactants may be employed. The reaction may be conducted at a temperature in the range of from 20° to about 110° C for a period of time of from about 15 minutes to about 5 hours; however, the reaction is generally conducted at the reflux temperature of the particular solvent employed for about one and ½ hours. The product is usually obtained in the form of an acid addition salt (VIa) from which the free amine (VI) can be generated by known neutralization methods (See general synthetic Method A). The following equation illustrates this reaction employing a mineral acid, $HR^1$:

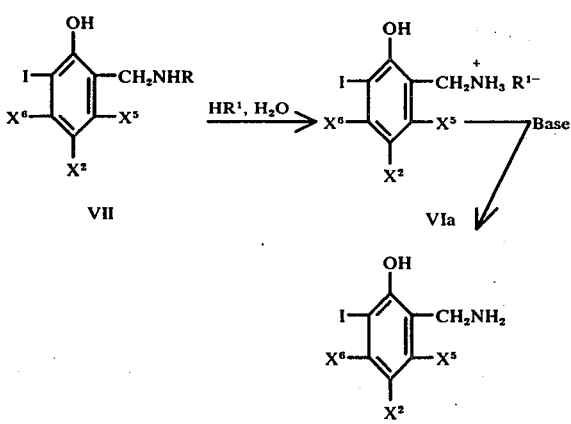

wherein $X^2$, $X^5$, $X^6$ and R are as previously defined.

Preparation of the requisite substituted 2-iodophenol (VIII) is accomplished by iodinating the corresponding substituted phenol (IX) using either of the two procedures described below. In the first procedure, the starting substituted phenol (IX) is treated with mercuric acetate in an aqueous medium such as water-acetic acid-ethanol at a temperature of 20° to 100° C, particularly at 80° to 85° C, for a period of 1 to 2 hours and then allowed to react with sodium chloride to afford 2-chloromercuri derivative (X). Treatment of X with a solution of iodine in a suitable solvent such as acetic acid, tetrahydrofuran, dioxane and the like added portionwise over a period of 1 to 2 hours provides the desired 2-iodophenol (VIII). This procedure is illustrated in the following equation:

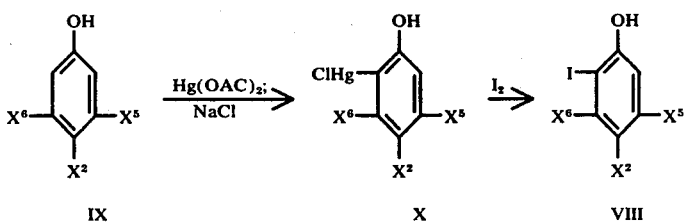

in which $X^2$, $X^5$ and $X^6$ are as previously defined.

In the second procedure, starting phenol IX is converted directly to 2-iodophenol VIII by treatment of IX with a solution of iodine monochloride in a suitable solvent such as acetic acid, tetrahydrofuran, dioxane and the like, particularly acetic acid, at a temperature sufficiently high to maintain solvent reflux for a period of from 2 to 10 hours. This procedure is illustrated in the following equation:

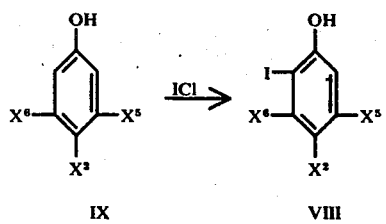

wherein $X^2$, $X^5$ and $X^6$ are as previously defined.

wheein $X^2$, $X^5$ and $X^6$ are as previously defined,; R is an acyl radical, for example, formyl,haloacetyl such as chloroacetyl and the like, carbamoyl, mononuclear aroyl such as benzoyl and the like, hydroxy substituted mononuclear aroly such as o-hydroxybenzoyl and the like, trihalomethylcarbonyl such as trichloromethylcarbonyl and the like; and $R^{1-}$ is the anion derived from an acid, for example, a mineral acid such as hydrochloric acid, hydrobromic acid, hydriodic acid, sulfuric acid and the like.

The required intermediate N-(2-hydroxy-3-iodo-4,5,6-substituted benzyl)carboxamide (VII) may be prepared by treating an appropriately substituted 2-iodophenol (VIII) with an N-(hydroxymethyl)carboxamide, for example, N-hydroxymethylurea, 2-halo-N-(hydroxymethyl)acetamides such as 2-chloro-N-(hydroxymethyl)acetamide and the like, an N-(hydroxymethyl)mononuclear arylcarboxamide such as N-(hydroxymethyl)benzamide and the like, an N-(hydroxymethyl)-hydroxy substituted arylcarboxamide such as N-(hydroxymethyl)-salicylamide and the like or an N-(hydroxymethyl)trihaloacetamide such as N-(hydroxymethyl)trichloroacetamide and the like, in the presence of a strong mineral acid such as hydrochloric acid, sulfuric acid and the like. The reaction may be conducted employing an excess of the mineral acid as the solvent or with a solvent which is either inert or substantially inert to the reactants employed, for example, a lower alkanol such as ethanol and the like or a lower alkanoic acid such as acetic acid and the like. The following equation illustrates this process:

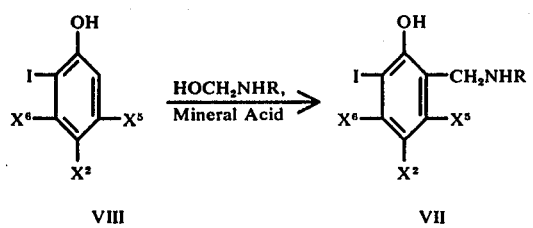

Typical of the instant products of this invention which may be prepared by synthetic Method B are:

2-Aminomethyl-4-(1-methylethyl)-6-iodophenol hydrochloride; and

2-Aminomethyl-4-(1,1-dimethylethyl)-6-iodophenol hydrochloride.

The examples which follow illustrate the substituted 2-aminomethyl-6-iodophenols of this invention and the methods by which they are prepared. However, the examples are illustrative only and it will be apparent to those having ordinary skill in the art that all of the products embraced by formula I, supra, may also be prepared in an analogous manner by substituting the appropriate starting materials for those set forth in the examples.

EXAMPLE 1

Preparation of 2-Aminomethyl-4-(1,1-dimethylethyl)-6-iodophenol Hydrochloride

Step A: Preparation of 2-chloromercuri-4-(1,1-dimethylethyl)phenol

Mercuric acetate (63.6 g., 0.2 mole) is dissolved in water (1200 ml.) and acetic acid (36 g.) is added. A solution of 4-(1,1-dimethylethyl)phenol (42 g., 0.3 mole) in warm 95% alcohol (60 ml.) is added to the aqueous mixture. A curdy precipitate forms. The mixture then is heated at 80°–85° C. for one hour. The curdy precipitate disappears and a heavy colorless oil forms which soon solidifies (I). The hot supernatant layer is decanted, heated to dissolve the precipitate that forms on slight cooling, and a solution of sodium chloride (35 g.) in water (150 ml.) is added with stirring. The precipitate (II) that separates on cooling is collected and air dried. The solid (I) is collected, air dried and dissolved in 2.5% sodium hydroxide (1870 ml.). The solution is filtered and acidified with 6N hydrochloric acid. The white precipitate (III) is collected and air dried. The solids I, II and III, is collected and air dried. The solids I, II and III, are combined and extracted with two 250 ml. portions of boiling absolute ethanol. The combined extracts are evaporated to dryness. The residue is extracted with one 270 ml. and one 150 ml. portion of dry benzene. The combined filtrates are concentrated to 150 ml. and allowed to cool to obtain 23.7 g. of 2-chloromercuri-4-(1,1-dimethylethyl)phenol, m.p. 157°–160° C.

Step B: Preparation of 2-Iodo-4-(1,1-dimethylethyl)phenol

2-Chloromercuri-4-(1,1-dimethylethyl)phenol (23.1 g., 0.06 mole) is dissolved in acetic acid (225 ml.) and a solution of iodine (15.24 g., 0.06 mole) in acetic acid (100 ml.) is added portion-wise during 1½ hours. The initial color of iodine disappears after addition of each portion. Sodium bisulfite is added to remove any excess iodine. The red precipitate of mercury halide is removed by filtration and the filtrate is poured into water (800 ml.). A red gum that soon solidifies is formed. The solid is collected, dissolved in ether and the solution again filtered to remove the solid mercury salts. The ether solution is washed with a potassium iodide solution until the washing gives no precipitate with hydrogen sulfide indicating the absence of mercury. The ether solution is dried over sodium sulfate and evaporated to obtain 14.62 g. of 2-iodo-4-(1,1-dimethylethyl)phenol, m.p. 71°–73° C.

Alternate Preparation of 2-Iodo-4-(1,1-dimethylethyl)phenol

A solution of iodine monochloride (82.6 g., 0.51 mole) in acetic acid (125 ml.) is added slowly in a portion-wise manner to a stirred solution of 4-(1,1-dimethylethyl)phenol (75 g., 0.50 mole) in acetic acid (250 ml.) providing a dark reaction mixture which is heated at reflux for 6 hours. After cooling to room temperature, the reaction mixture is poured into ice water (2 l.) containing sufficient sodium bisulfite to consume any iodine present. The resulting slurry is vigorously stirred for ½ hour at ambient temperature and filtered. The collected tan solid is washed with cold (−20° C.) petroleum ether (200 ml.) to afford 124 g. of the 2-iodo-4-(1,1-dimethylethyl)phenol, m.p. 70°–72° C., which is identical to an authentic sample prepared in Step B above.

Step C: Preparation of 2-Aminomethyl-4-(1,1-dimethylethyl)-6-iodophenol hydrochloride To a freshly prepared solution of 2-iodo-4-(1,1-dimethylethyl)phenol (5.5 g., 0.02 mole) in a mixture of acetic acid (27 ml.) and sulfuric acid (3 ml.) is added powdered 2-chloro-N-(hydroxymethyl)acetamide (2.5 g., 0.02 mole) with stirring at 20° C over a 10 minute period. After 2.5 hours the orange solution is poured into water (200 ml.). The 2-chloro-N-[2-hydroxy-3-iodo-5-(1,1-dimethylethyl)benzyl]-acetamide which precipitates is collected, dried by suction and dissolved in ethanol (75 ml.). Concentrated hydrochloric acid (15 ml.) is added and the mixture is refluxed for two hours. The mixture is concentrated to one-half its original volume and allowed to cool. The resulting precipitate (1.4 g.), which is unhydrolyzed 2-chloro-N-[2-hydroxy-3-iodo-5-(1,1-dimethylethyl)benzyl]acetamide, is collected. The filtrate is concentrated to 25 ml. and, upon cooling, crude 2-aminomethyl-4-(1,1-dimethylethyl)-6-iodophenol hydrochloride (4 g.) separates which upon crystallization from a mixture of ethanol and ether affords substantially pure 2-aminomethyl-4-(1,1-dimethylethyl)-6-iodophenol hydrochloride (2.5 g.), m.p. 200°–201° (dec.).

Elemental analysis for $C_{11}H_{17}ClINO$:
Calc.: C, 38.67; H, 5.02; N, 4.20; Found: C, 39.19; H, 5.03; N, 4.20.

By substituting for the 2-chloro-N-(hydroxymethyl)acetamide of Example 1, Step C, an equimolar quantity of N-(hydroxymethyl)urea, N-(hydroxymethyl)benzamide, N-(hydroxymethyl)salicylamide, N-(hydroxymethyl)trichloroacetamide, N-(hydroxymethyl)formamide and by following substantially the procedure described therein, there is obtained the N-[2-hydroxy-3-iodo-5-(1,1-dimethylethyl)benzyl]derivative of urea, benzamide, salicylamide, trichloroacetamide and formamide, respectively, each of which upon treatment with hydrochloride acid affords 2-aminomethyl-4(1,1-dimethylethyl)-6-iodophenol hydrochloride.

EXAMPLE 2

Alternate preparation of 2-aminomethyl-4-(1,1-dimethylethyl)-6-iodophenol hydrochloride

Step A: Preparation of 2-aminomethyl-4-(1,1-dimethylethyl)phenol hydrochloride A mixture of 4-(1,1-dimethylethyl)phenol (75 g., 0.50 mole), 2-chloro-N-(hydroxymethyl)acetamide (61 g., 0.50 mole) and 96% sulfuric acid (50 ml.) in acetic acid (500 ml.) is stirred at 20° C for 4 hours and then poured into ice water (2 l.) providing a heterogenous mixture. After decanting the aqueous solution, the insoluble white gum is extracted with ether. The organic extract is washed with water and saturated brine and evaporated in vacuo leaving a residual oil. A solution of the latter in 12N hydrochloric acid-ethanol (1:1; 400 ml.) is heated at reflux for 4 hours, diluted with 12N hydrochloric acid (200 ml.) and slowly cooled to −20° C. The deposited white crystalline solid is collected to provide pure 2-aminomethyl-4-(1,1- dimethylethyl)phenol hydrochloride (55 g.), m.p. 227°–229° C (dec.).

Elemental analysis for $C_{11}H_{18}ClNO$:
Calc.: C, 61.24; H, 8.41; N, 6.49; Found: C, 61.55; H, 8.50; N, 6.43.

Step B: Preparation of 2-Aminomethyl-4-(1,1-dimethylethyl)-6-iodophenol hydrochloride To a solution of 2-aminomethyl-4-(1,1-dimethylethyl)phenol hydrochloride (215 g., 1.0 mole) in water (1.6 l.) is added a solution of iodine monochloride (165 g., 1.0 mole) in 3N hydrochloric acid (800 ml.). The resulting reaction mixture is stirred at 20° C for 3 hours and then cooled to −20° C whereupon solid is deposited. The deposited solid is collected and crystallized from ethanol 12N-hydrochloric acid (1:1) to give the desired 2-aminomethyl-4-(1,1-dimethylethyl)-6-iodophenol hydrochloride (277 g.), m.p. 200°–201° C (dec.).

EXAMPLE 3

Preparation of 2-Aminomethyl-4-(1-methylethyl)-6-iodophenol hydrochloride

Step A: Preparation of 2-Iodo-4-(1-methylethyl)phenol 4-(1-Methylethyl)phenol (27.2 g., 0.20 moles) is dissolved in acetic acid (100 ml.). Iodine monochloride (32.5 g., 0.20 mole) in acetic acid (50 ml.) is then added slowly. The dark mixture is refluxed for 6 hours, cooled and poured into cold water (1 l.) containing a little sodium bisulfite. The black oil that separates is extracted with ether and the extract is washed with water and saturated brine and dried over magnesium sulfate. The ether is evaporated and the residue is purified by distillation to obtain 2-iodo-4-(1-methylethyl)phenol (26 g.), b.p. 137°–140° C (15 mm.).

Elemental analysis for $C_9H_{11}IO$:
Calc.: C, 41.89; H, 4.23 Found: C, 41.69; H, 4.62.

Step B: Preparation of 2-Aminomethyl-4-(1-methylethyl)-6-iodophenol hydrochloride 2-Iodo-4-(1-methylethyl)phenol (13.1 g., 0.05 mole) is dissolved in a mixture of acetic acid (50 ml.) and 96% sulfuric acid (5 ml.) and powdered 2-chloro-N-(hydroxymethyl)acetamide (6.15 g., 0.05 mole) is added during 10 minutes with stirring at 20° C. The solution is stirred for 2.5 hours and then added to 300 ml. of water. The crude solid (18 g.) is collected and refluxed in ethanol (25 ml.)-hydrochloric acid (10 ml.) for 2 hours. The solid (7.5 g.) that separates on cooling, namely 2-aminomethyl-4-(1-methylethyl)-6-iodophenol hydrochloride, is purified by crystallization from ethanol 12N-hydrochloric acid (7:3) to obtain 2-aminomethyl-4-(1-methylethyl)-6-iodophenol hydrochloride (7 g.), m.p. 211°–212° C (dec.).

Elemental Analysis for $C_{10}H_{15}ClINO$:
Calc.: C, 36.66; H, 4.62; N, 4.28 Found: C, 36.51; H, 4.54; N, 4.14.

EXAMPLE 4

Preparation of 2-Aminomethyl-4-(1,1-dimethylpropyl)-6-iodophenol hydrochloride Step A: Preparation of 2-aminomethyl-4-(1,1-dimethylpropyl)-6-iodophenol hydrochloride A mixture of 4-(1,1-dimethylpropyl)phenol (32.8 g., 0.2 mole) and 2-chloro-N-(hydroxymethyl)acetamide (24.6 g., 0.2 mole) in acetic acid (200 ml.) and 96% sulfuric acid (20 ml.) is stirred at 20° for 12 hours and then poured into cold water (1 l.). The solid that separates is extracted with ether and the ether extract is washed with water and salt brine and evaporated to dryness. The oily residue is dissolved in a mixture of 12N hydrochloric acid (100 ml.) and ethanol (100 ml.). The mixture is refluxed for 7 hours. The mixture then is evaporated to dryness under reduced pressure. The residue is triturated with dry ether to obtain a sticky white solid that is dissolved in hot ethanol (50 ml.) and precipitated in the cold by addition of ether (800 ml.). The solid is then crystallized from ethanol - 12N hydrochloric acid (1:10) to obtain 2-aminomethyl-4-(1,1-dimethylpropyl)phenol hydrochloride (17 g.), m.p. 191°–192° C.

Elemental analysis for $C_{12}H_{18}ClNO$:
Calc.: C, 62.73; H, 8.77: N, 6.10; Found: C, 62.80; H, 8.76; N, 6.21.

Step B: Preparation of 2-Aminomethyl-4-(1,1-dimethylpropyl)-6-iodophenol hydrochloride 2-Aminomethyl-4-(1,1-dimethylpropyl)phenol hydrochloride (4.6 g., 0.02 mole) is dissolved in water (15 ml.) and a solution of iodine monochloride (3.28 g.) in 3N hydrochloric acid (10 ml.) is added. The mixture is kept for 3 hours and then cooled to −10° C. The solid that separates is crystallized from ethanol-12N hydrochloric acid (1:10) to obtain 2-aminomethyl-4-(1,1-dimethylpropyl)-6-iodophenyl hydrochloride (4.15 g.), m.p. 203°–204° C (dec.).

Elemental analysis for $C_{12}H_{17}ClINO$:
Calc.: C, 40.53; H, 5.38; N, 3.94; Found: C, 40.77, H, 5.31: N, 3.97.

EXAMPLE 5

Preparation of 2-Aminomethyl-3-methoxy-4-(1,1-dimethylethyl)-6-iodophenol hydrochloride Step A: Preparation of 2-Chloro-4-(1,1-dimethylethyl)-5-methoxyphenol To a solution of 2-chloro-5-methoxyphenol (15.8 g., 0.10 mole) in benzene (30 ml.) and concentrated sulfuric acid (0.5 ml.) isobutylene (28.1 g., 0.5 mole) is added with stirring at 20°–25° C over a period of five hours. The mixture then is extracted with a 5% sodium hydroxide solution. The basic extract is acidified with dilute hydrochloric acid and the oil that separates is extracted with benzene. The benzene extract is dried over magnesium sulfate, filtered and the benzene removed. The residue is distilled to obtain a pale yellow oil (12.5 g.), b.p. 102°–103° C/1 mm. which contains 12% starting material and 88% of 2-chloro-4-(1,1-dimethylethyl)-5-methoxyphenol as determined by gas-liquid chromatography.

Step B: Preparation of 2-Aminomethyl-3-methoxy-4-(1,1-dimethylethyl)-6-chlorophenol hydrochloride By following substantially the procedure described in Example 4, Step A, and by substituting 2-chloro-4-(1,1-dimethylethyl)-5-methoxyphenol (12.5 g., 0.058 mole) for the 4-(1,1-dimethylethyl)phenol described therein, there is obtained, after recystallization from a mixture of ethanol and concentrated hydrochloric acid (4:5), 2.85 g. of 2-aminomethyl-3-methoxy-4-(1,1-dimethylethyl)-6-chlorophenol hydrochloride, m.p. 212°–213° C (dec.).

Elemental analysis for $C_{12}H_{19}Cl_2NO_2$:
Calc.: C, 51.44; H, 6.83; N, 5.00; Found: C, 51.50; H, 6.86; N, 4.81.

Step C: Preparation of 2-Aminomethyl-3-methoxy-4-(1,1-dimethylethyl)-phenol hydrochloride A solution of 2-aminomethyl-3-methoxy-4-(1,1-dimethylethyl)-6-chlorophenol hydrochloride (5.6 g., 0.02 mole) in 1% aqueous sodium hydroxide (250 ml.) is hydrogenated in a Parr apparatus at room temperature in the presence of 5% palladium/carbon (1 g.) and at a pressure of 30 p.s.i. until the theoretical quantity (1 molar equivalent) of hydrogen is consumed whereupon the catalyst is removed by filtration. Concentrated hydrochloric acid is added to the clear filtrate until pH 2 is reached and the acidic solution is then filtered to remove a tiny amount of white powder. Basicification of the clear filtrate with 15N ammonium hydroxide affords a precipitate which is collected and crystallized from a mixture of ethanol and 12N hydrochloric acid to yield the desired 2-aminomethyl-3-methoxy-4-(1,1-dimethylethyl)phenol hydrochloride.

Step D: Preparation of 2-aminomethyl-3-methoxy-4-(1,1-dimethylethyl)-6-iodophenol hydrochloride This compound is prepared essentially by the method as described in Example 2, Step B, except that the 2-aminomethyl-4-(1,1-dimethylethyl)phenol hydrochloride is replaced by an equimolar quantity of 2-aminomethyl-3-methoxy-4-(1,1-dimethylethyl)phenol hydrochloride. Thereby is obtained after crystallization of the crude product from ethanol-12N hydrochloric acid (2:1), the pure 2-aminomethyl-3-methoxy-4-(1,1-dimethylethyl)-6-iodophenol hydrochloride.

EXAMPLE 6

Preparation of 2-Aminomethyl-4-propyl-6-iodophenol hydrochloride

By following exactly the same procedures described in Example 2 but beginning with an equimolar quantity of 4-propylphenol rather than 4-(1,1-dimethylethyl)-phenol, there are obtained in order:
Step A, 2-Aminomethyl-4-propylphenol hydrochloride, m.p. 169°–170° C (dec.); and
Step B, 2-Aminomethyl-4-propyl-6-iodophenol hydrochloride, m.p. 200°–201° C (dec.).

EXAMPLE 7

Preparation of 2-Aminomethyl-4-butyl-6-iodophenol hydrochloride

By following exactly the same procedures described in Example 2 but beginning with 4-butylphenol rather than 4-(1,1-dimethylethyl)phenol, there are obtained in order:
Step A, 2-Aminomethyl-4-butylphenol hydrochloride; and
Step B, 2-Aminomethyl-4-butyl-6-iodophenol hydrochloride.

EXAMPLE 8

Preparation of 2-Aminomethyl-4-(2-methylpropyl)-6-iodophenol hydrochloride

The synthesis of this compound is carried out by the procedures of Example 2 except that 4-(2-methylpropyl)-phenol is used in Step A instead of 4-(1,1-dimethylethyl)-phenol. Thus, there are obtained in succession:
Step A, 2-Aminomethyl-4-(2-methylpropyl)phenol hydrochloride; and
Step B, 2-Aminomethyl-4-(2-methylpropyl)-6-iodophenol hydrochloride.

EXAMPLE 9

Preparation of 2-Aminomethyl-4-(1-methylpropyl)-6-iodophenol hydrochloride

By following exactly the same procedures described in Example 2 but beginning with 4-(1-methylpropyl)-phenol rather than 4-(1,1-dimethylethyl)phenol, there are obtained in succession:
Step A, 2-Aminomethyl-4-(1-methylpropyl)phenol hydrochloride, m.p. 188°–189° C (dec.); and
Step B, 2-Aminomethyl-4-(1-methylpropyl)-6-iodophenol hydrochloride, m.p. 189°–190° C (dec.).

EXAMPLE 10

Preparation of 2-Aminomethyl-4-pentyl-6-iodophenol hydrochloride

By following exactly the same procedures described in Example 4 but beginning with 4-pentylphenol instead of 4-(1,1-dimethylpropyl)phenol, there are obtained in order:
Step A, 2-Aminomethyl-4-pentylphenol hydrochloride; and
Step B, 2-Aminomethyl-4-pentyl-6-iodophenol hydrochloride.

EXAMPLE 11

Preparation of 2-Aminomethyl-4-(1-methylbutyl)-6-iodophenol hydrochloride

The synthesis of the title compound is carried out by the procedures of Example 4 except that 4-(1-methylbutyl)-phenol is used in Step A rather than 4-(1,1-dimethylpropyl)-phenol. Thus, there are obtained in order:
Step A, 2-Aminomethyl-4-(1-methylbutyl)phenol hydrochloride; and
Step B, 2-Aminomethyl-4-(1-methylbutyl)-6-iodophenol

EXAMPLE 12

Preparation of 2-Aminomethyl-4-(3-methylbutyl)-6-iodophenol hydrochloride

By following exactly the same procedures described in Example 4 but beginning with 4-(3-methylbutyl)- phenol instead of 4-(1,1-dimethylpropyl)phenol, there are obtained in succession:
Step A, 2-Aminomethyl-4-(3-methylbutyl)phenol hydrochloride; and
Step B, 2-Aminomethyl-4-(3-methylbutyl)-6-iodophenol hydrochloride.

EXAMPLE 13

Preparation of 2-Aminomethyl-4-(1,2-dimethylpropyl)-6-iodophenol hydrochloride

By following essentially the procedures described in Example 4 but beginning with 4-(1,2-dimethylpropyl)phenol instead of 4-(1,1-dimethylpropyl)phenol, there are obtained in order:
Step A, 2-Aminomethyl-4-(1,2-dimethylpropyl)phenol hydrochloride; and
Step B, 2-Aminomethyl-4-(1,2-dimethylpropyl)-6-iodophenol hydrochloride.

EXAMPLE 14

Preparation of 2-Aminomethyl-4-(2,2-dimethylpropyl)-6-iodophenol hydrochloride

The synthesis of this compound is effected by the procedures of Example 4 except that 4-(2,2-dimethylpropyl)phenol is used in Step A rather than 4-(1,1-dimethylpropyl)phenol. Thus, there are successively obtained:
Step A, 2-Aminomethyl-4-(2,2-dimethylpropyl)phenol hydrochloride; and
Step B, 2-Aminomethyl-4-(2,2-dimethylpropyl)-6-iodophenol hydrochloride.

EXAMPLE 15

Preparation of 2-Aminomethyl-4-(1-ethylpropyl)-6-iodophenol hydrochloride

By following essentially the procedures as described in Example 4 but beginning with 4-(1-ethylpropyl)phenol rather than 4-(1,1-dimethylpropyl)phenol, there are obtained in order:
Step A, 2-Aminomethyl-4-(1-ethylpropyl)phenol hydrochloride; and
Step B, 2-Aminomethyl-4-(1-ethylpropyl)-6-iodophenol hydrochloride.

EXAMPLE 16

Preparation of 2-Aminomethyl-3,5-dimethyl-4-(1,1-dimethylethyl)-6-iodophenol hydrochloride Step A: Preparation of 3,5-Dimethyl-4-(1,1-dimethylethyl)phenol This compound is prepared essentially by the process as described in Example 5, Step A, except that the 2-chloro-5-methoxyphenol is replaced by an equimolar quantity of 3,5-dimethylphenol. Distillation (in vacuo) of the crude product affords 3,5-dimethyl-4-(1,1-dimethylethyl)phenol.

Step B: Preparation of 2-Aminomethyl-3,5-dimethyl-4-(1,1-dimethylethyl)phenol hydrochloride This compound is prepared essentially by the method described in Example 2, Step A, except that the 4-(1,1-dimethylethyl)phenol used therein is replaced by an equimolar quantity of 3,5-dimethyl-4-(1,1-dimethylethyl)phenol. This method affords 2-aminomethyl-3,5-dimethyl-4-(1,1-dimethylethyl)phenol hydrochloride.

Step C: Preparation of 2-Aminomethyl-3,5-dimethyl-4-(1,1-dimethylethyl)-6-iodophenol hydrochloride This compound is synthesized using essentially the same procedure described in Example 2, Step B, except that the 2-aminomethyl-4-(1,1-dimethylethyl)phenol hydrochloride is replaced by an equimolar quantity of 2-aminomethyl-3,5-dimethylethyl)phenol hydrochloride. Crystallization of the crude product from ethanol - 12N hydrochloric acid (2:1) provides 2-aminomethyl-3,5-dimethyl-4-(1,1-dimethylethyl)-6-iodophenol hydrochloride.

EXAMPLE 17

Preparation of 2-Aminomethyl-3,5-dimethoxy-4-(1,1-dimethylethyl)-6-iodophenol hydrochloride Step A: Preparation of 3,5-dimethoxy-4-(1,1-dimethylethyl)phenol This compound is prepared essentially by the process as described in Example 5, Step A, except that the 2-chloro-5-methoxyphenol is replaced by an equimolar quantity of 3,5-dimethoxyphenol. Vacuum distillation of the crude product gives 3,5-dimethoxy-4-(1,1-dimethylethyl)phenol.

Step B: Preparation of 2-Aminomethyl-3,5-dimethoxy-4-(1,1-dimethylethyl)phenol hydrochloride This compound is prepared essentially by the method described in Example 2, Step A, except that the 4-(1,1-dimethylethyl)phenol used therein is replaced by an equimolar quantity of 3,5-dimethoxy-4-(1,1-dimethylethyl)phenol; thereby is obtained 2-aminomethyl-3,5-dimethoxy-4-(1,1-dimethylethyl)phenol hydrochloride.

Step C: Preparation of 2-Aminomethyl-3,5-dimethoxy-4-(1,1-dimethylethyl)-6-iodophenol hydrochloride This compound is synthesized using essentially the same procedure described in Example 2, Step B, except that the 2-aminomethyl-4-(1,1-dimethylethyl)phenol hydrochloride is replaced by an equimolar quantity of 2-aminomethyl-3,5-dimethoxy-4-(1,1-dimethylethyl)phenol hydrochloride. Crystallization of the crude product from ethanol - 12N hydrochloric acid (2:1) affords 2-aminomethyl-3,5-dimethoxy-4-(1,1-dimethylethyl)-6-iodophenol hydrochloride as essentially colorless crystals.

EXAMPLE 18

Preparation of 2-Aminomethyl-4-(1,1-dimethylethyl)-5-ethyl-6-iodophenol hydrochloride Step A: Preparation of 3-Ethyl-4-(1,1-dimethylethyl)phenol This compound is prepared essentialy by the method as described in Example 5, Step A, except that the 2-chloro-5-methoxy phenol is replaced by 3-ethylphenol. Distillation of the resulting crude product affords 3-ethyl-4-(1,1-dimethylethyl)phenol.

Step B: Preparation of 2-Aminomethyl-4-(1,1-dimethylethyl)-5-ethylphenol hydrochloride This compound is prepared essentially by the method as described in Example 4, Step A, except that the 4-(1,1-dimethylethyl) phenol is replaced by 3-ethyl-4-(1,1-dimethylethyl)phenol. Thereby is obtained 2-aminomethyl-4-(1,1-dimethylethyl)-5-ethyl phenol hydrochloride.

Step C: Preparation of 2-Aminomethyl-4-(1,1-dimethylethyl)-5-ethyl-6-iodophenol hydrochloride This compound is prepared essentially by the method as described in Example 2, Step B, except that the 2-aminomethyl-4-(1,1-dimethylethyl)phenol hydrochloride is replaced by 2-aminomethyl-4-(1,1-dimethylethyl)-5-ethyl phenol hydrochloride. Thereby is obtained 2-aminomethyl-4-(1,1-dimethylethyl)-5-ethyl-6-iodophenol hydrochloride.

EXAMPLE 19

Preparation of 2-Aminomethyl-4-(1,1-dimethylethyl)-5-ethoxy-6-iodophenol hydrochloride

Step A: Preparation of 3-Ethoxy-4-(1,1-dimethylethyl)phenol

This compound is prepared essentially by the method as described in Example 5, Step A, except that the 2-chloro-5-methoxy phenol is replaced by 3-ethoxyphenol. Distillation of the resulting crude product affords 3-ethoxy-4-(1,1-dimethylethyl)phenol.

Step B: Preparation of 2-Aminomethyl-4-(1,1-dimethylethyl)-5-ethoxyphenol hydrochloride This compound is prepared essentially by the method as described in Example 4, Step a, except that the 4-(1,1-dimethylethyl) phenol is replaced by 3-ethoxy-4-(1,1-dimethylethyl)phenol. Thereby is obtained 2-aminomethyl-4-(1,1-dimethylethyl)-5-ethoxy phenol hydrochloride.

Step C: Preparation of 2-aminomethyl-4-(1,1-dimethylethyl)-5-ethoxy-6-iodophenol hydrochloride This compound is prepared essentially by the method as described in Example 2, Step B, except that the 2-aminomethyl-4-(1,1-dimethylethyl)phenol hydrochloride is replaced by 2-aminomethyl-4-(1,1-dimethylethyl)-5-ethoxy-phenol hydrochloride. Thereby is obtained 2-aminomethyl-4-(1,1-dimethylethyl)-5-ethoxy-6-iodophenol hydrochloride.

EXAMPLE 20

Preparation of 2-Aminomethyl-4-(1,1-dimethylethyl)-6-iodophenol

A freshly-prepared solution of 2-aminomethyl-4-(1,1-dimethylethyl)-6-iodophenol hydrochloride (5 g., 15 millimole) in water (100 ml.) is stirred at room temperature and basicified to pH ca.8 by addition of 15N ammonium hydroxide (excess) providing a fine slurry which is stirred at room temperature for 10 minutes and filtered. The collected solid is washed with water and dried in vacuo at 80° C. over phosphorous pentoxide for 2 hours to provide 2-aminomethyl-4-(1,1-dimethylethyl)-6-iodophenol as a colorless solid (4.2 g.), m.p. 146°–146.5° C (dec.).

Elemental analysis for $C_{11}H_{16}INO$:
Calc.: C, 43.30; H, 5.29; N, 4.59; Found: C, 43.40; H, 5.56; N, 4.64.

EXAMPLE 21

Preparation of 2-Aminomethyl-4-(1,1-dimethylethyl)-6-iodophenol isethionate hemihydrate To a freshly-prepared solution of 2-aminomethyl-4-(1,1-dimethylethyl)-6-iodophenol (1.95 g., 6.5 millimole) in 2-propanol (20 ml.) is added 6.5N isethionic acid (1 ml., 6.5 milliequivalents) at room temperature. Upon diluting the resulting solution with ether (100 ml.), a white solid precipitates and is collected to given 2.4 g., m.p. 160°–163° C. (den.). Crystallization (twice) of this solid from 2-propanol-ether (2:5 70 ml.) affords 2-aminomethyl-4-(1,1-dimethylethyl)-6-iodophenol isethionate-hemihydrate as colorless crystals (1.93 g.), m.p. 166°–167.5° C.(dec.).

Elemental analysis for $C_{13}H_{22}INO_5S \cdot \frac{1}{2}H_2O$;
Calc.: C, 35.54; H, 5.27; N, 3.15; Found: C, 35.42; H, 5.30; N, 3.21.

By substituting an equimolar quantity of hydrochloric acid, hydrobromic acid, hydriodic acid, sulfuric acid, methane sulfonic acid and phosphoric acid for the isethionic acid employed in the above example, there are obtained 2-aminomethyl-4-(1,1-dimethylethyl)-6-iodophenol hydrochloride, 2-aminomethyl-4-(1,1-dimethylethyl)-6-iodophenol hydrobromide, 2-aminomethyl-4-(1,1-dimethylethyl)-6-iodophenol hydriodide, 2-aminomethyl-4-(1,1-dimethylethyl)-6-iodophenol sulfate, 2-aminomethyl-4-(1,1-dimethylethyl)-6-iodophenol methane sulfonate and 2-aminomethyl-4-(1,1-dimethylethyl)-6-iodophenol phosphate, respectively.

The novel compounds of this invention are antihypertensive, diuretic and saluretic agents which can be administered in a wide variety of therapeutic dosages in conventional vehicles as, for example, by oral administration in the form of a tablet or capsule, or by intravenous injection. Also the daily dosage of the products may be varied over a wide range varying from 5 to 2,000 mg. The product is preferably administered in subdivided doses in the form of scored tablets containing 5, 10, 25, 50, 100, 150, 250 and 500 milligrams (most preferably 10 to 500 mg.) of the active ingredient for the symptomtic adjustment of the dosage to the patient to be treated. These dosages are well below the toxic or lethal dose of the products.

A suitable unit dosage form of the products of this invention can be formulated by mixing 50 milligrams of a substituted 2-aminomethyl-6-iodophenol (I) or a suitable pharmaceutically acceptable salt thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capusles may be employed. Compressed tablets, pills, or other desired unit dosages can be prepared to incorporate the compounds of this invention by conventional methods and, if desired, can be made up as elixirs or as injectable solutions by methods well known to pharmacists.

It is also within the scope of this invention to combine two or more of the compounds of this invention in a unit dosage form or to combine one or more of the compounds of this invention with other known diuretics and saluretics such as amiloride hydrochloride or with other desired therapeutic and/or nutritive agents in dosage unit form.

The following example is included to illustrate the preparation of a representative dosage form:

EXAMPLE 22

Dry-filled capsules containing 50 mg. of active ingredient per capsule

|  | Per Capsule |
| --- | --- |
| 2-Aminomethyl-4-(1,1-dimethylethyl)-6-iodophenol hydrochloride | 50 mg. |
| Lactose | 149 mg. |
| Magnesium Stearate | 1 mg. |
| Capsule (Size No. 1) | 200 mg. |

The 2-aminomethyl-4-(1,1-dimethylethyl)-6-iodophenol hydrochloride is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It wll be apparent from the foregoing description that the substituted 2-aminomethyl-6-iodophenols (I) and the pharmaceutically acceptable salts thereof of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula:

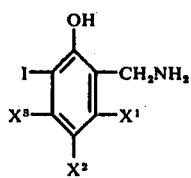

wherein
$X^1$ is hydrogen, methyl or methoxy;
$X^2$ is lower alkyl containing from 3 to 5 carbon atoms;
$X^3$ is hydrogen, methyl, ethyl, methoxy or ethoxy or a non-toxic pharmaceutically acceptable salt thereof.

2. A compound of the formula:

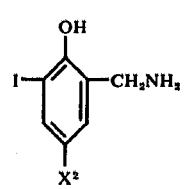

wherein
$X^2$ is lower alkyl containing from 3 to 5 carbon atoms or a non-toxic pharmaceutically acceptable acid addition salt thereof.

3. A compound of the formula:

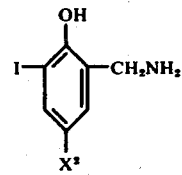

wherein $X^2$ is a 4 or 5 carbon atom branched alkyl group wherein the branching occurs on the carbon atom attached to the ring or a non-toxic pharmaceutically acceptable acid addition salt thereof.

4. 2-Aminomethyl-4-(1,1-dimethylethyl)-6-iodophenol or a non-toxic pharmaceutically acceptable acid addition salt thereof.

5. 2-Aminomethyl-4-(1,1-dimethylethyl)-6-iodophenol.

6. A compound according to claim 4 wherein the pharmaceutically acceptable salt is the hydrochloride salt thus forming 2-aminomethyl-4-(1,1-dimethylethy)-6-iodophenol hydrochloride.

7. 2-Aminomethyl-4-(1,1-dimethylpropyl)-6-iodophenol or a non-toxic pharmaceutically acceptable acid addition salt thereof.

8. 2-Aminomethyl-4(1-methylpropyl)-6-iodophenol or a non-toxic pharmaceutically acceptable acid addition salt thereof.

9. A pharmaceutical composition useful in the treatment of hypertension and edema which comprises from about 10 mg. ot 500 mg. of a compound of the formula:

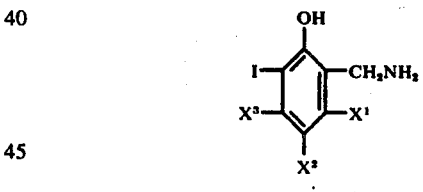

wherein
$X^1$ is hydrogen, methy or methoxy;
$X^2$ is lower alkyl containing from 3 to 5 carbon atoms;
$X^3$ is hydrogen, methyl, ethyl, methoxy or ethoxy or a non-toxic pharmaceutically acceptable salt thereof in an inert carrier.

10. A pharmaceutical composition useful in the treatment of hypertension and edema which comprises from about 10 mg. ot 500 mg. of a compound of the formula:

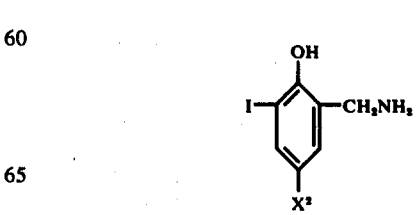

wherein $X^2$ is lower alkyl containing from 3 to 5 carbon atoms or a non-toxic pharmaceutically acceptable acid addition salt thereof in an inert carrier.

11. A pharmaceutical composition useful in the treatment of hypertension and edema which comprises from about 10 mg. to 500 mg. of a compound of the formula:

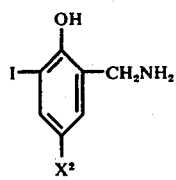

wherein $X^2$ is a 4 or 5 carbon atom branched alkyl group wherein the branching occurs on the carbon atom attached to the ring or a non-toxic pharmaceutically acceptable acid addition salt thereof in an inert carrier.

12. A pharmaceutical composition useful in the treatment of hypertension and edema which comprises from about 10 mg. ot 500 mg. of 2-aminomethyl-4-(1,1-dimethylethyl)-6-iodophenol or a non-toxic pharmaceutically acceptable acid addition salt thereof in an inert carrier.

13. A pharmaceutical composition according to claim 12 wherein the compound is 2-aminomethyl-4-(1,1-dimethylethyl)-6-iodophenol.

14. A pharmaceutical composition according to claim 12 wherein the compound is 2-aminomethyl-4-(1,1-dimethylethyl)-6-iodophenol hydrochloride.

* * * * *